United States Patent [19]

Seiler et al.

[11] 4,224,233
[45] Sep. 23, 1980

[54] PROCESS FOR THE PRODUCTION OF ALKYLSILANES

[75] Inventors: Claus-Dietrich Seiler, Rheinfelden; Hans-Joachim Vahlensieck, Wehr, both of Fed. Rep. of Germany

[73] Assignee: Dynamit Nobel Aktiengesellschaft, Troisdorf, Fed. Rep. of Germany

[21] Appl. No.: 26,633

[22] Filed: Apr. 3, 1979

[30] Foreign Application Priority Data

Apr. 8, 1978 [DE] Fed. Rep. of Germany ........ 2815316

[51] Int. Cl.² ................................................ C07F 7/08
[52] U.S. Cl. .................................................. 556/478
[58] Field of Search .................................. 260/448.2 E

[56] References Cited

U.S. PATENT DOCUMENTS 3,706,777  12/1972  Seiler et al. ................... 260/448.2 E Primary Examiner—Paul F. Shaver
Attorney, Agent, or Firm—Sprung, Felfe, Horn, Lynch & Kramer

[57] ABSTRACT

An improved process for the preparation of alkylsilanes and/or alkylsilanes substituted at the alkyl group by an addition reaction in the presence of a platinum or palladium supported catalyst wherein the reaction mixture is heated to its boiling point, condensed and the condensate contacts the catalyst, the improvement residing in vaporizing the reaction mixture and maintaining the vapors in out of contact relationship with respect to the platinum or palladium supported catalyst and contacting the reaction mixture only after it has condensed with the platinum or palladium supported catalyst and recovering the condensed reaction product.

13 Claims, No Drawings

PROCESS FOR THE PRODUCTION OF ALKYLSILANES

BACKGROUND OF THE INVENTION

SUMMARY OF THE INVENTION

The present invention relates to a process for the preparation of alkylsilanes which are prepared by an addition reaction with the aid of platinum or palladium catalysts.

DISCUSSION OF THE PRIOR ART

It is known to react hydrogen silanes with carbon compounds containing olefinic double bonds in the presence of platinum compounds or metallic platinum, which may be present in the substrate or applied to various supports, to alkylsilanes. Such processes are described in U.S. Pat. Nos. 2,637,738 and 2,632,013, in German Pat. Nos. 11 69 936, 10 69 148 and 11 65 028, and in German patent applications DAS 11 56 073 and 12 10 844, for example. It is further known from U.S. Pat. No. 3,706,777 to carry out the addition reaction in such a way that the carrier material impregnated with the catalyst is disposed above the reaction mixture, between the latter and a condensing apparatus. The condensate from the condensing apparatus is caused to trickle over the carrier material while at the same time vaporous starting material flows from below through the reaction mixture from the receiver for the reactants. When allyl chloride, for example, is used as olefinic component and reacted by this procedure with trichlorosilane, yields of 3-chloropropyl trichlorosilane of about 64 percent will be obtained. About 35 mol percent of the allyl chloride will react due to the β-cleavage, with formation of propylene and silicon tetrachloride. Moreover, with this operating procedure space-time yields are unsatisfactory.

Thus, the problem has been to improve the space-time yield in the addition reaction and at the same time reduce the formation of by-products. It became an object of this invention, therefore, to provide such a process.

SUMMARY OF THE INVENTION

The foregoing objects are provided in accordance with this invention by performing the addition reaction of U.S. Pat. No. 3,706,777 in such a manner that the reaction mixture is evaporated and rises to a cooling means, situated above the supported catalyst. The rising vapors of this reaction mixture are maintained in out of contact relationship with respect to the supported platinum or palladium catalyst. These nobel metal catalysts are disposed above the boiling reaction mixture. The vapors of the reaction mixture are condensed in the cooling means and this condensed reaction mixture is permitted to fall through the supported catalyst bed where the addition reaction takes place. The reaction product and non reacted reaction mixture fall through a by-pass such as in the form of a sluice or air lock into the still with the boiling reaction mixture. The boiling point of the reaction mixture rises up to the boiling point of the desired alkylsilane, so that the non-reacted part of the reaction mixture can be reevaporated and condensed in the condensation zone once again and caused to fall through the supported mass of catalyst. The catalyst in turn can be a supported catalyst of platinum or palladium supported on an inert support such as activated charcoal. The catalyst granules can themselves be disposed on a porous inert glass plate whereby the condensed reaction mixture fall through the granules of supported catalyst and the support for the granules to fall into the zone where the reaction mixture is once again vaporized.

In accordance with this invention, such a process is provided which can be practiced both at atmospheric pressure (normal pressure) and at above-atmospheric pressure. Even at atmospheric pressure a space-time yield of at least twice that of the process according to German Pat. No. 20 12 299 is obtained.

A particularly advantageous variant of the process consists in carrying out the reaction under pressure. Pressures of up to 50 bars may be employed. Even at pressures of up to 20 bars, an increase over the space-time yield at normal pressure will be obtained. In addition, operating at above-atmospheric pressure results in reduced formation of by-products and hence a further increase in the yield of desired end product. Thus, in the reaction of trichlorosilane with allyl chloride carried out with platinum catalysts, for example, only about 64 mol percent of the allyl chloride is converted every time to 3-chloropropyl trichlorosilane when normal pressure is employed, with some 36 mol percent of the allyl chloride being converted to α-methyl-β-chloroethyl trichlorosilane, which due to the β-cleavage decomposes to propylene and silicon tetrachloride. When in the process in accordance with the invention this reaction is carried out at superatmospheric pressure, as much as 83 to 84 mol percent of the allyl chloride is converted directly to 3-chloropropyl trichlorosilane while only about 17 to 16 mol percent of the allyl chloride entering into the reaction reacts to form propylene and silicon tetrachloride. The process in accordance with the invention is appropriately carried out in such a way that the starting materials are heated to ebullition in a suitable vessel and the vapors or gases both of the hydrogen silane and of the olefinic component are then conducted to a suitable condensing apparatus where they are condensed. In this flow to the condenser, the catalyst is bypassed, i.e., the vaporous reactants do not come in contact with the catalyst.

The catalyst is advantageously disposed on a suitable carrier material, which is preferably arranged in the form of a fixed bed above the boiling vessel for the starting materials, between the latter and the condensing apparatus. The reactants condensed in the condensing apparatus then trickle downwardly onto this catalyst bed through suitable feed members such as distributor plates. Thus, the catalyst bed is contacted by the reactants when the same is mainly in the form of a condensate, exiting the condenser.

In the catalyst bed the components react with evolution of heat. The reaction products emerge, together with excess, unconverted starting material, at the lower part of the bed. Through appropriate air locks or sluices, the reaction products and unconverted starting materials are returned to the still, from where the unconverted components are recycled to the process by evaporation. The end of the reaction is indicated by the fact that the reaction mixture boils at constant temperature and that the catalyst bed is no longer heated up.

The air locks between the catalyst bed and the collector, maintained at boiling temperature, are required in order to prevent starting material vapors from penetrating the catalyst bed from below. A suitable device for this purpose is the siphon, for example. Other suitable devices are known to the person skilled in the art.

A variant of the process in accordance with the invention consists in introducing the hydrogen-silane component into the apparatus, heating it to ebullition, and then commencing to add the olefinic component continuously or discontinuously. This procedure is indicated when pressure is employed, for example, or when a gaseous olefinic component is used. However, depending on the circumstances, it may be advantageous to reverse the procedure.

The hydrogen silanes which may be used in accordance with the invention comprise halogen silanes and organo-H-silanes, characterized by the formula $H_nSiR_{4-n}$, n being able to assume the values 1 to 3 and R representing an alkyl group of 1–8 carbon atoms, a vinyl group, phenyl, phenoxy, alkoxy of 1–8 carbon atoms and halogen. Examples of halogen silanes which can be reacted are trichlorosilane and dichlorosilane. Among the hydrogen containing organohalosilanes which can be reacted are methylhydrogendichlorosilane, dimethylhydrogenchlorosilane and diethylhydrogenchlorosilane. The organo-hydrogen alkoxysilanes which can be used in accordance with the invention include trimethoxy- and dimethoxyhydrogensilane, triethoxy- and diethoxyhydrogensilane and triphenoxysilane. Further suitable hydrogen silanes are, for example, trimethylhydrogensilane, diethyldihydrogensilane, dibutyldihydrogensilane, diphenyldihydrogensilane and vinylhydrogendimethoxysilane.

Preferably mixed substituted hydrogen silanes where halogen is one of the substituents are reacted in accordance with the invention such as vinylhydrogendichlorosilane or methyl- and ethylhydrogendichlorosilane.

The olefins generally have 2 to 10 carbon atoms in the chain and are preferably ethylene and propylene. However, pentene-1, octene-1, butadiene and acetylene can also be used in accordance with the invention. Among the usable substituted olefins are allylbenzene, styrene and divinylbenzene. For these substituted olefins the double bond should not be in the terminal position; for example, heptene-3 and tert. amylene may also be used. Olefin hydrocarbons are particularly contemplated.

Halogenous olefins such as vinyl chloride, trichloroethylene, 1,1-difluoroethylene, 1,1,1-trifluoropropylene, allyl chloride, 3-chlorobutene-1 or cyclic unsaturated hydrocarbons such as cyclohexene and vinylcyclohexene can be used as starting compounds, as can alkenyl esters such as allyl acetate and vinyl acetate.

In the event that one of the reactants should decompose or tend to polymerize at elevated temperatures, it will be advisable to operate at subatmospheric pressure.

Generally speaking, the temperature will depend upon the nature of the reactants and the prevailing pressure. Broadly speaking, the temperature can vary between 0° and 250° C., preferably between 50° and 180° C., with pressure and temperature being somewhat inversely proportional.

In operation at above-atmospheric pressure, the latter is appropriately brought about by increasing the system temperature accordingly. Care should be taken that the temperature at the point of condensation is not substantially below the boiling point of the system at the predetermined fixed pressure as otherwise the desired system pressure will collapse.

In order to more fully illustrate the nature of the invention and the manner of practicing the same, the following examples are presented:

EXAMPLES

Example 1 (Comparative Example)

A 2-liter three-necked flask is inserted in a heating jacket. Into the middle one of the three necks there is set a glass tube of 20 cm in length (inside diameter about 4.5 cm) to one side of which a ground socket is fused and to the other side a ground cone. Above the cone, a glass grate is fused into the interior of the tube, and on this grate the catalyst is placed. A low-temperature condenser is set onto the tube containing the catalyst. The system is closed toward the outside by means of a nitrogen scavenging arrangement. A thermometer is inserted in one of the outer necks of the flask to permit monitoring of the still temperature.

Into the glass tube which is to hold the catalyst, 150 ml of activated carbon which contains 0.1 weight percent of platinum (particle size 1 to 2 mm, bulk density 450 g/l) and which has been broken in over an extended period of time is introduced. As the term is used here, a broken-in catalyst is one which has been employed in a plant on the industrial scale in the reaction of at least 700 mols of allyl chloride with 770 mols of trichlorosilane per liter of catalyst and therefore has a maximum of activity.

4.4 mols of trichlorosilane and 4.0 mols of allyl chloride are then charged to the flask. A cooling solution of about $-32°$ C. is fed to the condenser. Through mild heating of the flask, the catalyst is exposed to a gas stream consisting of trichlorosilane and allyl chloride coming from below while from above unreacted trichlorosilane and allyl chloride condensed at the condenser surface trickles onto the catalyst.

After reflux sets in at the condenser, the heating current control is adjusted just enough for the system to remain at constant reflux. After a constant sump temperature of 85° C. has been attained and heat has been applied for 27 hours, the experiment is discontinued and the sump product is worked up by distillation.

543 g (2.56 mols) of 3-chloropropyl trichlorosilane is obtained, which corresponds to a yield of 64 percent based on the allyl chloride which entered into the reaction.

Example 2

The apparatus described in Example 1 is modified as follows:

1. The 2-liter three-necked flask is replaced with a four-necked flask of the same size.

2. Two glass tubulatures 1 cm in diameter are fused into the glass tube holding the catalyst, one of them below the glass grating supporting the catalyst, the other below the ground socket in which the ground cone of the low-temperature condenser is inserted. Moreover, a TEFLON stopper is inserted in the opening of the ground cone of the glass tube to close the latter downwardly.

3. From one of the tubulatures of the four-necked flask, a connecting glass tube is run to the uppermost of the two glass tubulatures.

4. From a further tubulator of the four-necked flask, a connecting glass tube is run to one of the legs of a U-tube. The other leg of the U-tube (1 cm in diameter) is connected through a glass tube to the lower glass tubulature of the catalyst carrier tube (located below the glass grating).

Apart from this, all specifications given in Example 1 for the construction of the apparatus used in the experiment apply here, too.

The flask is filled with 4.4 mols of trichlorosilane and 4.0 mols of allyl chloride and then heated by switching on the current for the heating jacket. The trichlorosilane and allyl chloride vapors which evolve rise in the connecting tube mentioned under 3 above between the four-necked flask and the upper glass tubulature of the catalyst carrier column and then reach the low-temperature condenser, where they are condensed. From there the condensate reaches the activated carbon/charcoal where the reaction takes place. After passing through the catalyst bed, the mixture of reaction product and unconverted starting components is recycled through the U-tube which acts as a siphon, to the flask, from where the unconverted components are again fed to the reaction zone.

After a uniform reflux has been established in the condenser, the heating-current control is set at the value at which the experiment of Example 1 was run, and the heating-current control is adjusted as indicated therein. After a heating time of 8.5 hours, a constant sump temperature of 87° C. is reached, and the experiment is discontinued.

The sump product is worked up by distillation. 552 g (2.61 mols) of 3-chloropropyl trichlorosilane is obtained, which corresponds to a yield of 65.3 percent based on the allyl chloride which entered into the reaction. By this operating procedure, a 3.1-fold increase in the space-time yield is obtained in this case over the procedure employed in Example 1.

Example 3

Analogously to Example 2, an apparatus is constructed from steel. The still has a volume of about 9 liters and is heated with steam by means of an immersion heater.

The condenser has a surface area of about 1 m$^2$ and is operated with water as cooling medium. At the start of the experiment, no water is fed to the condenser.

The nitrogen blanket above the condenser in Example 2 is dispensed with. The apparatus is sealed against pressure. A pressure gauge and a thermometer are mounted on the still, and their values are recorded by a recorder. As catalyst charge, 750 ml of the activated charcoal/platinum catalyst was used. The height of the bed is about 8 cm. In the center of the catalyst bed is a temperature-measuring point whose values are recorded by a recorder. 40 mols (5410 g) of trichlorosilane is introduced into the steel still. The system is sealed against pressure. By applying steam to the coils of the immersion heater, the apparatus is brought to an internal pressure of 8 bars within 10 minutes. Then the cooling-water feed/supply line is carefully opened and held open until that point where the pressure within the apparatus just begins to drop.

As soon as the catalyst bed is about to reach the temperature of the sump (about 95° C.), the introduction of allyl chloride by means of a pressure metering pump is started. The rise in temperature at the measuring point located in the catalyst bed indicates the start of the reaction.

2,280 g (30 mols) of allyl chloride is introduced over a period of 4 hours. About another 10 minutes is allowed for further reaction. The temperature drop which then sets in at the platinum/activated charcoal measuring point indicates the end of the reaction. The contents of the bulb are then cooled by applying cooling water to the coils of the immersion heater and then drawn off.

The reaction product so drawn off is then analyzed by gas chromatography. It is found that about 87 percent of the allyl chloride charged has been converted to 3-chloropropyl trichlorosilane. Working up of the reaction product by distillation yields 5,270 g (24.9 mols) of 3-chloropropyl trichlorosilane, which represents a yield of 83 percent, based on the allyl chloride which entered into the reaction.

With this operating procedure, the space-time yield is increased 3-fold, and the yield, based on the allyl chloride used, increased absolutely by almost 20 percent, and relatively by nearly 28 percent.

Example 4

In the experimental apparatus made of steel described in Example 3, 40 mols (5,410 g) of trichlorosilane are reacted with 30 mols (1,260 g) of propylene by the same procedure. The propylene is fed to the system directly from a pressure cylinder.

The reaction pressure is between 10 and 12 bars; the reaction temperature is between 110° and 120° C. The charging time is about one hour.

After the temperature at the measuring point in the activated charcoal/platinum catalyst has been allowed to drop, the reaction product is drawn off after cooling and subjected to analysis by gas chromatography. No residual content of unconverted propylene is determined.

Working up of the crude product by distillation yields 4,899 g (27.6 mols) of propyltrichlorosilane, which corresponds to a yield of about 92 percent, based on the propylene which was charged into the reaction system.

Example 5

In the experimental apparatus of steel described in Example 3, 40 mols (5,140 g) of trichlorosilane are reacted with 30 mols (2,100 g) of n-pentane by the procedure employed in that example.

The liquid pentene is fed into the system by means of a pressure metering pump.

The reaction pressure is between 8 and 10 bars, the reaction temperature between 110° and 115° C. The charging time is about 1 hour and 10 minutes.

After the temperature at the measuring point in the activated charcoal/platinum catalyst has been allowed to drop, the reaction mixture is drawn off and subjected to analysis by gas chromatography. No content of unconverted pentene is determined.

Working up of the crude product by distillation yields 5,842 g (28.5 mols) of pentyltrichlorosilane, which represents a yield of about 95 percent, based on the n-pentene-1 which was charged into the reaction system.

What is claimed is:

1. In a process for the preparation of an alkylsilane or substituted alkylsilane substituted in the alkyl group by an addition reaction in the presence of a platinum or palladium catalyst, deposited on a carrier wherein the catalyst is disposed above the reaction mixture and below a cooling system from which condensate from the cooling system drops onto said catalyst, and reaction component is vaporized, rises to said cooling means and is condensed therein, the improvement which comprises maintaining the rising vapors of said reaction component in out of contact relationship with respect to said catalyst.

2. A process according to claim 1 wherein reaction mixture formed by contact at said catalyst together with at least a portion of unreacted mixture are collected through an air lock or siphon in a collecting vessel, vaporized and the resultant vapors are passed to the cooling means while being maintained in out of contact relationship while in vaporous form with said catalyst.

3. A process according to claim 1 wherein a siphon is disposed between the supported catalyst and the boiling reaction mixture.

4. A process according to claim 1 carried out at a pressure in the range of 0.1 to 50 bars absolute.

5. A process according to claim 1 carried out at normal (atmospheric) pressure.

6. A process according to claim 1 wherein the process is carried out at superatmospheric pressure up to 50 bars absolute.

7. A process according to claim 1 wherein the process is conducted up to a pressure of 20 bars absolute.

8. A process according to claim 1 wherein a hydrogen silane is reacted with an organic compound containing olefinic unsaturation.

9. A process according to claim 8 wherein the hydrogen silane is a silicon hydride.

10. A process according to claim 8 wherein the hydrogen silane is an organosilane containing only organo groups and hydrogen atoms as substituents bonded to the silicon atom.

11. A process according to claim 8 wherein the hydrogen silane is an organohalohydrogen silane.

12. A process according to claim 8 wherein the olefinically unsaturated compound has between 2 and 10 carbon atoms in the chain.

13. A process according to claim 12 wherein the hydrogen silane is selected from the group consisting of methyl, hydrogen dichlorosilane, dimethylhydrogen chlorosilane, diethyl hydrogenchlorosilane, trimethoxy hydrogen silane, dimethoxy hydrogen silane, triethoxy hydrogen silane, diethoxy hydrogen silane, triphenoxy silane, trimethyl hydrogen silane, diethyldihydrogen silane, dibutyldihydrogen silane, diphenyldihydrogen silane, vinyl hydrogen dimethoxy silane, vinyl hydrogen dichlorosilane, methyl hydrogen dichlorosilane, ethyl hydrogen dichlorosilane, trichlorosilane and dichlorosilane and the olefinically unsaturated organic compound is selected from the group consisting of ethylene, propylene, pentene-1, octene-1, butadiene, acetylene, allylbenzene, styrene, divinylbenzene, vinylchloride, trichloroethylene, 1,1-difluoroethylene, 1,1,1-trifluoropropylene, allyl chloride, 3-chlorobutene-1, cyclohexene, vinylcyclohexene and alkyl esters.

* * * * *

UNITED STATES PATENT AND TRADEMARK OFFICE
CERTIFICATE OF CORRECTION

PATENT NO. : 4,224,233
DATED : September 23, 1980
INVENTOR(S) : CLAUS-DIETRICH SEILER and HANS-JOACHIM VAHLENSIECK It is certified that error appears in the above—identified patent and that said Letters Patent is hereby corrected as shown below:

| Column | Line | |
|---|---|---|
| 2 | 23 | change "percen" to --percent--. |
| 4 | 65 | change "tubulator" to --tubulature-- |
| 6 | 43 | "pentane" should be --pentene-- |

Signed and Sealed this

Tenth Day of March 1981

[SEAL]

Attest:

RENE D. TEGTMEYER

Attesting Officer     Acting Commissioner of Patents and Trademarks